United States Patent
Shluzas

(10) Patent No.: US 6,673,074 B2
(45) Date of Patent: Jan. 6, 2004

(54) APPARATUS FOR RETAINING BONE PORTIONS IN A DESIRED SPATIAL RELATIONSHIP

(75) Inventor: Alan E. Shluzas, Millis, MA (US)

(73) Assignee: Endius Incorporated, Plainville, MA (US)

( * ) Notice: Subject to any disclaimer, the term of this patent is extended or adjusted under 35 U.S.C. 154(b) by 29 days.

(21) Appl. No.: 09/921,326

(22) Filed: Aug. 2, 2001

(65) Prior Publication Data

US 2003/0028191 A1 Feb. 6, 2003

(51) Int. Cl.$^7$ ............................................... A61B 17/70
(52) U.S. Cl. ............................................ 606/61; 606/73
(58) Field of Search ........................... 606/60, 61, 72, 606/73

(56) References Cited

U.S. PATENT DOCUMENTS

| | | | |
|---|---|---|---|
| 5,041,113 A | | 8/1991 | Biedermann et al. |
| 5,084,048 A | | 1/1992 | Jacob et al. |
| 5,129,899 A | * | 7/1992 | Small et al. ................ 606/61 |
| 5,520,690 A | | 5/1996 | Errico et al. |
| 5,531,746 A | | 7/1996 | Errico et al. |
| 5,613,968 A | | 3/1997 | Lin |
| 5,984,924 A | | 11/1999 | Asher et al. |
| 6,004,322 A | * | 12/1999 | Bernstein ................... 606/61 |
| 6,123,706 A | * | 9/2000 | Lange ........................ 606/61 |
| 6,187,005 B1 | * | 2/2001 | Brace et al. ................ 606/61 |
| 6,280,443 B1 | | 8/2001 | Gu et al. |

FOREIGN PATENT DOCUMENTS

FR  2796546 A1 * 1/2001 ........... A61B/17/70

OTHER PUBLICATIONS

Pending U.S. patent application Ser. No. 09/821,666 filed Mar. 29, 2001 entitled an Apparatus for Retaining Bone Portions in a Desired Spatial Relationship, Attorney Docket No. A31–5614.

* cited by examiner

Primary Examiner—Eduardo C. Robert
Assistant Examiner—Michael B. Priddy
(74) Attorney, Agent, or Firm—Tarolli, Sundheim, Covell & Tummino L.L.P.

(57) ABSTRACT

An apparatus (10) includes a member (12) and a fastener (16) that connects the member to a bone portion. The fastener (16) has a first end portion (22) engageable with the bone portion, a second end portion (26) extending through an opening (50) in the member (12), and an intermediate portion (32) engageable with the member between the first and second end portions. A connecting ring (42) connects the member (12) to the fastener (16). The connecting ring (42) extends into the opening (50) in the member (12). The connecting ring (42) has a passage (54) with a longitudinal axis (56) through which the second end portion (26) of the fastener (16) extends. A clamping member (28) engages the second end portion (26) of the fastener (16) and the connecting ring (42) to connect the connecting ring to the member (12) and connect the fastener to the connecting ring in any one of a plurality of angular positions relative to the connecting ring.

12 Claims, 2 Drawing Sheets

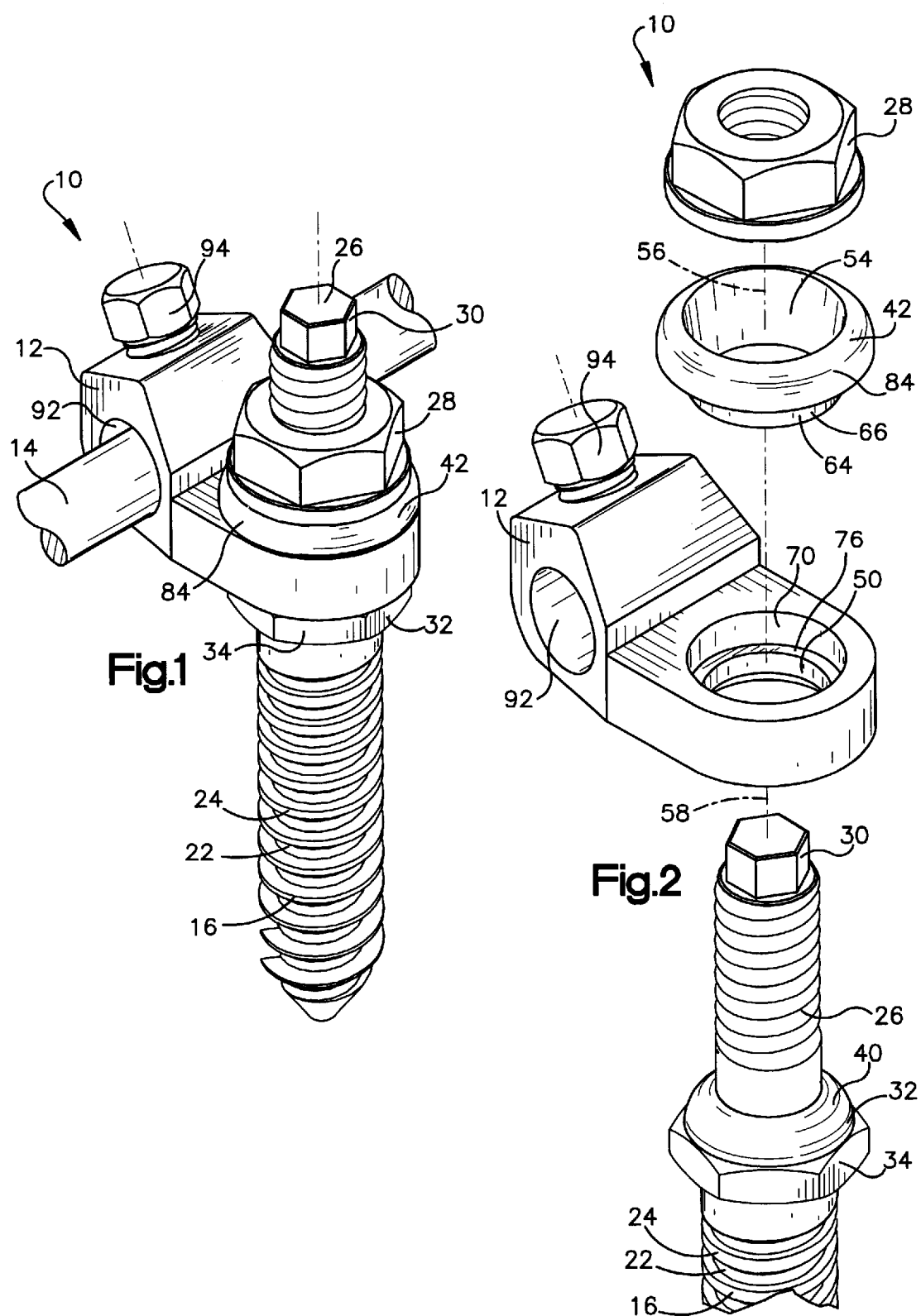

APPARATUS FOR RETAINING BONE PORTIONS IN A DESIRED SPATIAL RELATIONSHIP

TECHNICAL FIELD

The present invention relates to an apparatus which is used to retain bone portions, such as vertebrae of a spinal column, in a desired spatial relationship.

BACKGROUND OF THE INVENTION

A known apparatus for retaining vertebrae of a spinal column in a desired spatial relationship is disclosed in U.S. Pat. No. 5,613,968. U.S. Pat. No. 5,613,968 discloses an apparatus including a longitudinal member extendable along the spinal column. A fixation member connects the longitudinal member to a fastener connectable with a vertebra. A universal pad connects the fastener with the fixation member. The universal pad extends into the fixation member and the fastener extends through the universal pad. The universal pad has a protruding arcuate surface and a recessed arcuate surface concentric with the protruding arcuate surface. A clamping member is provided with a recessed arcuate surface engageable with the protruding arcuate surface on the universal pad. The fastener has a protruding arcuate surface engaging the recessed arcuate surface on the universal pad. The fastener is universally pivotable in any direction relative to the universal pad.

SUMMARY OF THE INVENTION

The present invention is an apparatus which is used to retain bone portions, such as vertebrae, in a desired spatial relationship. The apparatus includes a member connectable with a bone portion having an opening. A fastener which connects the member to the bone portion has a longitudinal axis. The fastener has a first end portion engageable with the bone portion, a second end portion extending through the opening in the member, and an intermediate portion engageable with the member between the first and second end portions. A connecting ring extends into the opening in the member and connects the member to the fastener.

The connecting ring has a passage with a longitudinal axis through which the second end portion of the fastener extends. The fastener is positionable in any one of a plurality of angular positions relative to the connecting ring so that the longitudinal axis of the fastener extends at any one of a plurality of angles to the longitudinal axis of the passage in the connecting ring. A clamping member engages the second end portion of the fastener and the connecting ring to connect the connecting ring to the member and connect the fastener to the connecting ring in any one of the plurality of angular positions relative to the connecting ring.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein:

FIG. 1 is a perspective view of an apparatus constructed in accordance with the present invention;

FIG. 2 is an exploded perspective view of a portion of the apparatus of FIG. 1.

DESCRIPTION OF THE INVENTION

Figure 3:
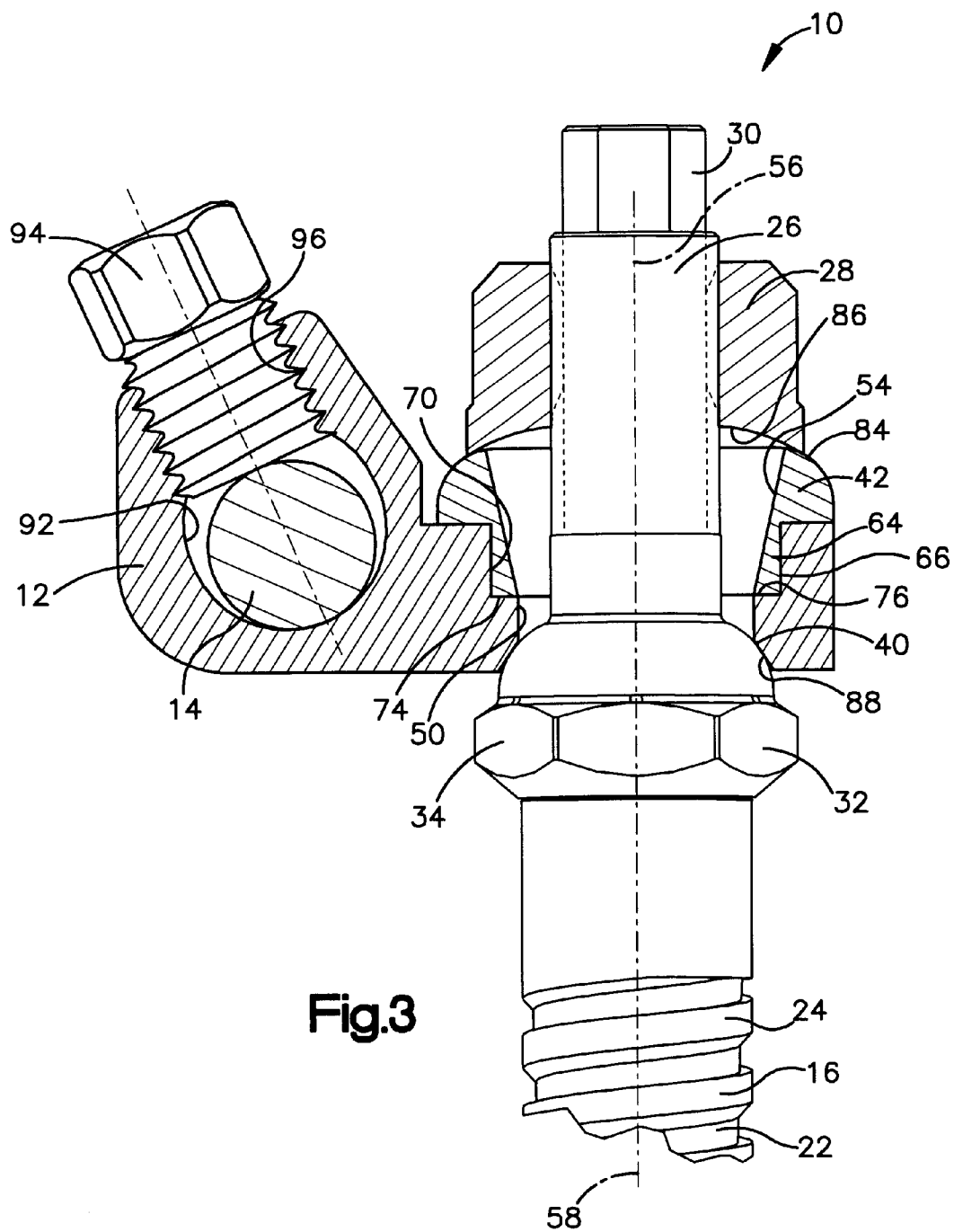
FIG. 3 is a sectional view of the apparatus of FIG. 1.

The present invention is directed to an apparatus for retaining bone portions, such as vertebrae of a spinal column, in a desired spatial relationship. FIGS. 1–3 illustrate an apparatus 10 constructed according to the present invention. The apparatus 10 includes a plurality of surgically implantable members 12, one of which is shown in FIGS. 1–3. The members 12 connect a rod 14 to bone portions (not shown), such as vertebrae of a spinal column, to maintain the bone portions in a desired spatial relationship. The rod 14 extends along the spinal column and has a length which is at least sufficient to enable the rod to span at least two vertebrae. The length of the rod 14 in any particular installation will depend on the number of vertebrae to be held in a desired spatial relationship relative to each other by the rod.

The spine rod 14 and member 12 (FIGS. 1 and 3) are connected to a vertebra by a fastener 16. The fastener 16 has a threaded inner end portion 22 having a course thread convolution 24 which engages the vertebra. An outer end portion 26 of the fastener 16 is provided with a relatively fine thread which engages an internal thread convolution on a clamping member or nut 28.

Wrenching flats 30 (FIGS. 2 and 3) are provided on the end portion 26 of the fastener 16. Torque may be applied to the flats 30 to turn the thread convolution 24 into the vertebra and/or apply a counter torque when the clamping member 28 is threaded onto the fastener 16. An intermediate portion 32 of the fastener 16 has wrenching flats 34. Torque is applied to the wrenching flats 34 to turn the threaded convolution 24 into the vertebra.

The intermediate portion 32 (FIG. 3) of the fastener 16 has an arcuate convex surface 40 which abuttingly engages the member 12. When the clamping member 28 is tightened, the member 12 is securely clamped against the surface 40 of the intermediate portion 32 to connect the member 12 to the fastener 16. The fastener 16 (FIGS. 1–3) is connected to the member 12 by a connecting ring 42. The member 12 includes an opening 50 into which the connecting ring 42 extends. The outer end portion 26 of the fastener 16 extends through the opening 50.

The connecting ring 42 (FIGS. 2–3) has a passage 54 with a longitudinal axis 56 through which the outer end portion 26 of the fastener 16 extends. The fastener 16 is positionable in any one of a plurality of angular positions relative to the connecting ring 42 so that a longitudinal axis 58 of the fastener extends at any one of a plurality of angles to the longitudinal axis 56 of the passage 54 in the connecting ring. More specifically, the fastener 16 is universally pivotable in any direction relative to the connecting ring 42.

The connecting ring 42 has an axially extending portion 64 which extends into the opening 50 in the member 12. A cylindrical outer surface 66 of the axially extending portion 64 frictionally engages a cylindrical surface 70 defining the opening 50 in the member 12. There is an interference fit between the axially extending portion 64 of the connecting ring 42 and the surface 70 defining the opening 50 to connect the connecting ring to the member 12. The connecting ring 42 (FIG. 3) has an axial end surface 74. The axial end surface 74 engages a radially extending surface 76 on the member 12 when the axially extending portion 64 extends into the opening 50. It is contemplated that the axial end surface 74 may not engage the surface 76. The axially extending portion 64 of the connecting ring 42 is pressed into the opening 50 in the member 12 to connect the connecting ring to the member. It is also contemplated that the connecting ring 42 could be formed as one piece with the member 12.

The connecting ring 42 (FIG. 3) has an arcuate convex surface 84. The arcuate convex surface 84 engages an arcuate concave surface 86 on the clamping member 28. The member 12 has an arcuate concave surface 88. The arcuate concave surface 88 on the member 12 engages the arcuate convex surface 40 on the intermediate portion 32 of the fastener 16. Accordingly, the fastener 16 is universally pivotable relative to the connecting ring 42.

The spine rod 14 (FIGS. 1 and 3) extends through a passage 92 in the member 12. A set screw or fastener 94 threadably engages an opening 96 in the member 12. The fastener 94 engages the rod 14 to clamp the rod to the member 12 in the passage 92.

When the spine rod 14 is to be connected to a vertebra, the fastener 16 is connected to the vertebra. The member 12 with the connecting ring 42 connected to the member is placed on the rod 14 and the fastener 16 with the fastener extending through the connecting ring 42. The fastener 16 is positioned in any one of the plurality of angular positions relative to the connecting ring 42.

Once the member 12 has been positioned relative to the fastener 16, the clamping member 28 is placed on the fastener. The clamping member 28 is threaded onto the fastener 16 to cause the member 12 to be clamped between the connecting ring 42 and the intermediate portion 32 of the fastener 16. The clamping member 28 also clamps the connecting ring 42 to the member 12. The set screw 94 is threaded into the opening 96 in the member 12 to clamp the spine rod 14 to the member.

Although the present invention is shown connecting a member 12 and a spine rod 14 to a vertebra, it is contemplated that the connecting ring 42 and the fastener 16 could be used to connect a plate to a vertebra of a spinal column. From the above description of the invention, those skilled in the art will perceive improvements, changes and modifications. Such improvements, changes and modifications within the skill of the art are intended to be covered by the appended claims.

Having described the invention, the following is claimed:

1. An apparatus comprising:
   a member connectable with a bone portion, said member having an opening;
   a fastener which connects said member to the bone portion having a longitudinal axis, said fastener having a first end portion engageable with the bone portion, a second end portion extending though said opening in said member, and an intermediate portion directly engageable with said member between said first and second end portions;
   a connecting ring which connects said member to said fastener, said connecting ring extending into said opening in said member, said connecting ring having a passage with a longitudinal axis through which said second end portion of said fastener extends, said fastener being positionable in any one of a plurality of angular positions relative to said connecting ring so that said longitudinal axis of said fastener extends at any one of a plurality of angles to said longitudinal axis of said passage in said connecting ring; and
   a clamping member engaging said second end portion of said fastener and said connecting ring to connect said connecting ring to said member and connect said fastener to said connecting ring in any one of said plurality of angular positions relative to said connecting ring.

2. An apparatus as defined in claim 1 wherein said fastener is universally pivotable in any direction relative to said connecting ring prior to said clamping member connecting said fastener to said connecting ring.

3. An apparatus as defined in claim 1 wherein said connecting ring engages said member with an interference fit.

4. An apparatus as defined in claim 1 wherein said member has a surface engageable with an axial end surface of said connecting ring.

5. An apparatus as defined in claim 4 wherein said member includes a radially extending surface engageable with said axial end surface of said connecting ring.

6. An apparatus as defined in claim 1 wherein said connecting ring has a tapered surface defining said passage through which said second end portion of said fastener extends.

7. An apparatus as defined in claim 1 wherein said member is connect able with a spinal rod extending along a spinal column.

8. An apparatus as defined in claim 7 wherein said member has a passage through which the spinal rod extends.

9. An apparatus comprising:
   a member connectable with a bone portion, said member having an opening;
   a fastener which connects said member to the bone portion having a longitudinal axis, said fastener having a first end portion engageable with the bone portion, a second end portion extending though said opening in said member, and an intermediate portion engageable with said member between said first and second end portions, said intermediate portion of said fastener having an arcuate surface engageable with an arcuate surface on said member;
   a connecting ring which connects said member to said fastener, said connecting ring extending into said opening in said member, said connecting ring having a passage with a longitudinal axis through which said second end portion of said fastener extends, said fastener being positionable in any one of a plurality of angular positions relative to said connecting ring so that said longitudinal axis of said fastener extends at any one of a plurality of angles to said longitudinal axis of said passage in said connecting ring; and
   a clamping member engaging said second end portion of said fastener and said connecting ring to connect said connecting ring to said member and connect said fastener to said connecting ring in any one of said plurality of angular positions relative to said connecting ring.

10. An apparatus as defined in claim 9 wherein said intermediate portion of said fastener has an arcuate convex surface engageable with an arcuate concave surface on said member.

11. An apparatus as defined in claim 9 wherein said connecting ring has an arcuate surface engageable with an arcuate surface on said clamping member.

12. An apparatus comprising:
   a member connectable with a bone portion, said member having an opening;
   a fastener which connects said member to the bone portion having a longitudinal axis, said fastener having a first end portion engageable with the bone portion, a second end portion extending though said opening in said member, and an intermediate portion engageable with said member between said first and second end portions;
   a connecting ring which connects said member to said fastener, said connecting ring extending into said opening in said member, said connecting ring having a passage with a longitudinal axis through which said second end portion of said fastener extends, said fastener being positionable in any one of a plurality of angular positions relative to said connecting ring so that said longitudinal axis of said fastener extends at any one of a plurality of angles to said longitudinal axis of said passage in said connecting ring;

a clamping member engaging said second end portion of said fastener and said connecting ring to connect said connecting ring to said member and connect said fastener to said connecting ring in any one of said plurality of angular positions relative to said connecting ring;

said member being connectable with a spinal rod extending along a spinal column;

said member having a passage through which the spinal rod extends; and a fastener engageable with the spinal rod to clamp the spinal rod to said member.

* * * * *